United States Patent [19]

Gould et al.

[11] Patent Number: 4,579,999

[45] Date of Patent: Apr. 1, 1986

[54] MULTISTAGE PROCESS FOR CONVERTING OXYGENATES TO LIQUID HYDROCARBONS WITH ALIPHATIC RECYCLE

[75] Inventors: Ronald M. Gould, Sewell; Samuel A. Tabak, Wenonah, both of N.J.

[73] Assignee: Mobil Oil Corporation, New York, N.Y.

[21] Appl. No.: 733,994

[22] Filed: May 14, 1985

Related U.S. Application Data

[63] Continuation-in-part of Ser. No. 692,261, Jan. 17, 1985, Pat. No. 4,543,435.

[51] Int. Cl.⁴ .............................................. C07C 1/20
[52] U.S. Cl. ............................... 585/312; 585/313; 585/315; 585/322; 585/327; 585/408; 585/469; 585/640
[58] Field of Search ............... 585/312, 313, 314, 315, 585/322, 327, 330, 408, 469, 640

[56] References Cited

U.S. PATENT DOCUMENTS

| | | | |
|---|---|---|---|
| 3,928,483 | 12/1975 | Chang et al. | 585/469 |
| 3,931,349 | 1/1976 | Kuo | 585/322 |
| 3,965,205 | 6/1976 | Garwood et al. | 585/415 |
| 3,969,426 | 7/1976 | Owen et al. | 585/322 |
| 4,025,576 | 5/1977 | Chang et al. | 585/640 |
| 4,058,576 | 11/1977 | Chang et al. | 585/640 |
| 4,431,856 | 2/1984 | Daviduk et al. | 585/469 |
| 4,433,185 | 2/1984 | Tabak | 585/312 |
| 4,450,311 | 5/1984 | Wright et al. | 585/413 |
| 4,456,779 | 6/1984 | Owen et al. | 585/415 |
| 4,482,772 | 11/1984 | Tabak | 585/254 |
| 4,497,968 | 2/1985 | Wright et al. | 585/304 |
| 4,504,691 | 3/1985 | Hsia et al. | 585/519 |
| 4,504,693 | 3/1985 | Tabak et al. | 585/520 |
| 4,506,106 | 3/1985 | Hsia et al. | 585/312 |
| 4,523,046 | 6/1985 | Gould et al. | 585/322 |
| 4,543,435 | 9/1985 | Gould et al. | 585/330 |

OTHER PUBLICATIONS

"Production of Chemicals from Methanol", Warren W. Kaeding and Stephen A. Butter, Journal of Catalysis, vol. 61, No. 1, Jan. 1980.

"Conversion of Methanol to Hydrocarbons", Margaret M. Wu and Warren W. Kaeding, Journal of Catalysis 88, 478-489 (1984).

*Primary Examiner*—Andrew H. Metz
*Assistant Examiner*—A. Pal
*Attorney, Agent, or Firm*—A. J. McKillop; M. G. Gilman; L. G. Wise

[57] ABSTRACT

A process for converting oxygenated feedstock, such as methanol, dimethyl ether or the like, to liquid hydrocarbons.

In the primary catalyst stage the feedstock is contacted with zeolite catalyst to produce $C_2$-$C_4$ olefins and $C_5+$ hydrocarbons.

In a secondary catalytic stage with oligomerization catalyst comprising medium-pore shape selective acidic zeolite at increased pressure converts $C_3+$ olefins to gasoline and/or distillate liquids.

The improvement is a technique for recovering lower alkene for recycle to the primary catalytic stage.

11 Claims, 5 Drawing Figures

MULTISTAGE PROCESS FOR CONVERTING OXYGENATES TO LIQUID HYDROCARBONS WITH ALIPHATIC RECYCLE

REFERENCE TO COPENDING APPLICATION

This application is a continuation-in-part of copending U.S. patent application Ser. No. 692,261, filed Jan. 17, 1985, now U.S. Pat. No. 4,543,435, incorporated herein by reference.

BACKGROUND OF THE INVENTION

This invention relates to an integrated system for converting oxygenates, such as methanol or dimethyl ether (DME), to liquid hydrocarbons. In particular it provides a continuous process for producing hydrocarbon products by converting the oxygenate feedstock catalytically to an intermediate lower olefinic stream and oligomerizing the olefins to produce distillate and gasoline.

In order to provide an adequate supply of liquid hydrocarbons for use as synfuels or chemical feedstocks, various processes have been developed for converting coal and natural gas to gasoline, distillate and lubricants. A substantial body of technology has grown to provide oxygenated intermediates, especially methanol. Large scale plants can convert methanol or similar aliphatic oxygenates to liquid fuels, especially gasoline. However, the demand for heavier hydrocarbons has led to the development of processes for increasing yield of diesel fuel by a multi-stage technique.

Recent developments in zeolite catalysts and hydrocarbon conversion processes have created interest in utilizing olefinic feedstocks, for producing $C_5+$ gasoline, diesel fuel, etc. In addition to the basic work derived from ZSM-5 type zeolite catalysts, a number of discoveries have contributed to the development of a new industrial process, known as Mobil Olefins to Gasoline/Distillate ("MOGD"). This process has significance as a safe, environmentally acceptable technique for utilizing feedstocks that contain lower olefins, especially $C_2-C_5$ alkenes. This process may supplant conventional alkylation units. In U.S. Pat. Nos. 3,960,978 and 4,021,502, Plank, Rosinski and Givens disclose conversion of $C_2-C_5$ olefins, alone or in admixture with paraffinic components, into higher hydrocarbons over crystalline zeolites having controlled acidity. Garwood et al have also contributed improved processing techniques to the MOGD system, as in U.S. Pat. Nos. 4,150,062, 4,211,640 and 4,227,992. The above-identified disclosures are incorporated herein by reference.

Conversion of lower olefins, especially propene and butenes, over HZSM-5 is effective at moderately elevated temperatures and pressures. The conversion products are sought as liquid fuels, especially the $C_5+$ aliphatic and aromatic hydrocarbons. Olefinic gasoline is produced in good yield by the MOGD process and may be recovered as a product or recycled to the reactor system for further conversion to distillate-range products. Operating details for typical MOGD units are disclosed in U.S. Pat. Nos. 4,445,031, 4,456,779 (Owen et al) and 4,433,185 (Tabak), incorporated herein by reference.

In addition to their use as shape selective oligomerization catalysts, the medium pore ZSM-5 type catalysts are useful for converting methanol and other lower aliphatic alcohols or corresponding ethers to olefins. Particular interest has been directed to a catalytic process ("MTO") for converting low cost methanol to valuable hydrocarbons rich in ethene and $C_3+$ alkenes. Various processes are described in U.S. Pat. Nos. 3,894,107 (Butter et al), 3,928,483 (Chang et al), 4,025,571 (Lago), 4,423,274 (Daviduk et al) and 4,433,189 (Young), incorporated herein by reference. It is generally known that the MTO process can be optimized to produce a major fraction of $C_2-C_4$ olefins. Prior process proposals have included a separation section to recover ethene and other gases from byproduct water and $C_5+$ hydrocarbon liquids. These oligomerization process conditions which favor the production of $C_{10}-C_{20}$ and higher aliphatics tend to convert only a small portion of ethene as compared to $C_3+$ olefins.

SUMMARY OF THE INVENTION

It has been discovered that methanol, DME or the like may be converted to liquid fuels, particularly distillate, in a multi-stage continuous process, with integration between the major process units providing an alkene-rich recycle stream. The initial stage MTO type process hydrocarbon effluent stream, after byproduct water separation, can be fed to the MOGD stage for conversion to heavier hydrocarbons. Ethene and $C_5+$ hydrocarbons may be recovered by interstage separation from the primary effluent or the secondary oligomerization stage gasoline product may be recovered for recycle to the MTO unit. Advantageously, the recycle is found to be reactive in the presence of ZSM-5 type catalysts and increase the yield of $C_3-C_4$ olefins and, ultimately, the overall distillate yield. This discovery is particularly useful for converting recycled gasoline in a fluidized bed MTO unit.

In a preferred embodiment, the invention provides methods and apparatus for an integrated continuous technique for converting oxygenated organic feedstock to liquid hydrocarbons comprising means for contacting the feedstock with zeolite catalyst in a primary fluidized bed catalyst stage at elevated temperature and moderate pressure to convert feedstock to hydrocarbons comprising $C_2-C_4$ olefins and $C_5+$ hydrocarbons;

cooling and separating effluent from the primary stage to recover a liquid hydrocarbon stream and a light hydrocarbon vapor stream rich in $C_2-C_4$ lower olefins;

pressurizing and contacting the light olefinic hydrocarbon stream in a secondary catalytic stage with oligomerization catalyst comprising medium-pore shape selective acidic zeolite at substantially increased pressure and moderate temperature to convert at least a portion of olefins to a heavier liquid hydrocarbon product stream comprising olefinic gasoline and distillate range liquids; and recovering an olefinic gasoline stream for recycle to the primary catalytic stage for conversion in the fluidized bed.

Advantageously, the primary and secondary stage catalyst comprises ZSM-5 type zeolite and light hydrocarbons are recycled to the primary stage at a rate of about 1 to 30 parts gasoline ($C_5-C_9$) per 100 parts by weight of hydrocarbon equivalent in the feedstock. By fractionating gaseous effluent separated from the primary staged effluent a light recycle gas stream may be recovered containing at least 90% of ethene from the primary catalytic stage and an olefinic stream rich in $C_3+$ olefins.

THE DRAWINGS

DESCRIPTION OF PREFERRED EMBODIMENTS

Figure 1:
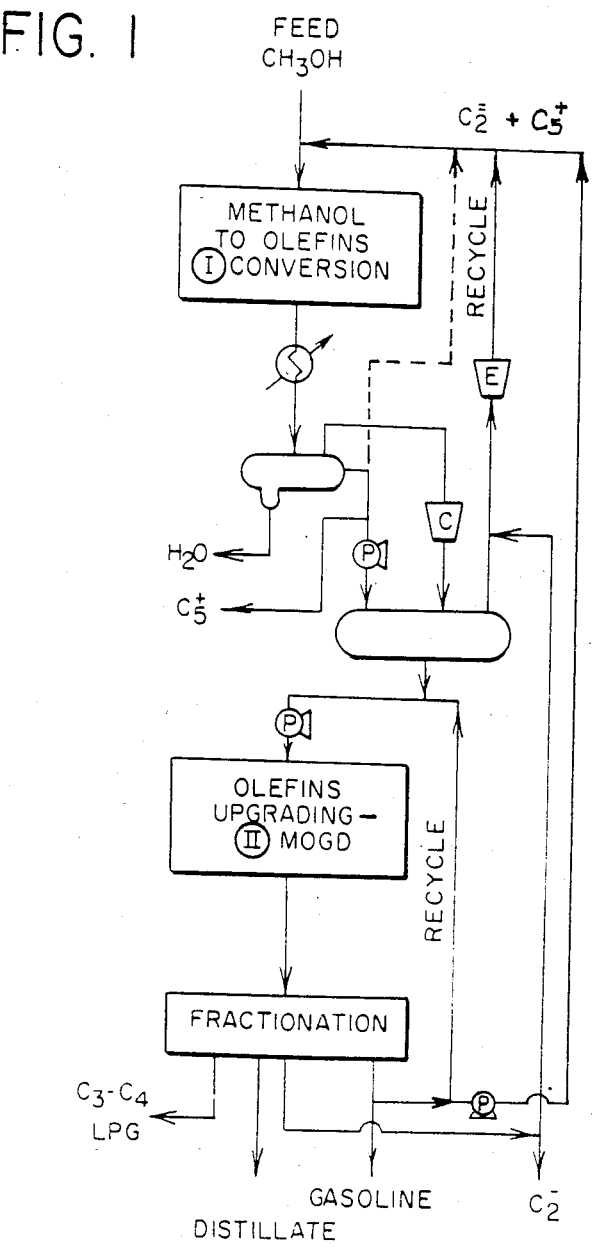
FIG. 1 is a process flow sheet showing the major unit operations and process streams.

Numerous oxygenated organic compounds may be contained in the feedstock material to be converted in the primary stage. Since methanol or its ether derivative (DME) are industrial commodities available from synthesis gas or the like, these materials are utilized in the description herein as preferred starting materials. It is understood by those skilled in the art that MTO-type processes can employ methanol, dimethylether and mixtures thereof, as well as other aliphatic alcohols, ethers, ketones and/or aldehydes. It is known in the art to partially convert oxygenates by dehydration, as in the catalytic reaction of methanol over gamma-alumina to produce DME intermediate. Typically, an equilibrium mixture ($CH_3OH \rightleftharpoons CH_3OCH_3 + H_2O$) is produced by partial dehydration. This reaction takes place in either conversion of methanol to lower olefins (MTO) or methanol to gasoline (MTG).

Catalyst versatility permits the same zeolite to be used in both the primary conversion stage (MTO) and secondary oligomerization stage (MOGD). While it is within the inventive concept to employ substantially different catalysts in these stages, it is advantageous to employ a standard ZSM-5 having a silica alumina molar ratio of 70:1.

The oligomerization catalysts preferred for use herein include the crystalline aluminosilicate zeolites having a silica to alumina ratio of at least 12, a constraint index of about 1 to 12 and acid cracking activity of about 160-200. Representative of the ZSM-5 type zeolites are ZSM-5, ZSM-11, ZSM-12, ZSM-22, ZSM-23, ZSM-35 and ZSM-38. ZSM-5 is disclosed and claims in U.S. Pat. No. 3,702,886 and U.S. Pat. No. Re. 29,948; ZSM-11 is disclosed and claimed in U.S. Pat. No. 3,709,979. Also, see U.S. Pat. No. 3,832,449 for ZSM-12; U.S. Pat. No. 4,076,979. Also, see U.S. Pat. No. 3,832,449 for ZSM-12; U.S. Pat. No. 4,076,842 for ZSM-23; U.S. Pat. No. 4,016,245 for ZSM-35 and U.S. Pat. No. 4,046,839 for ZSM-38. The disclosures of these patents are incorporated herein by reference. A suitable catalyst for fixed bed operation is HZSM-5 zeolite with 35 wt. % alumina binder in the form of cyclindrical extrudates of about 1-5 mm. These medium pore shape selective catalysts are sometimes known as porotectosilicates or "pentasil" catalysts.

Other catalysts and processes suitable for converting methanol/DME to lower olefins are disclosed in U.S. Pat. Nos. 4,393,265 (Bonifaz), 4,387,263 (Vogt et al.) and European Patent Application No. 0081683 (Marosi et al.), and ZSM-45. In addition to the preferred aluminosilicates, the borosilicate, ferrosilicate and "silicalite" materials may be employed. ZSM-5 type catalysts are particularly advantageous because the same material may be employed for dehydration of methanol to DME, conversion to lower olefins and oligomerization.

In this description, metric units and parts by weight are employed unless otherwise stated. Various reactor configurations may be used, including fluidized bed catalytic reactors, moving bed and fixed bed reactors.

Referring to FIG. 1, the process feedstock (methanol or DME, for instance) is fed to the primary stage I where it is converted to lower olefins and gasoline hydrocarbon plus water by dehydration of the oxygenated feedstock. Byproduct water is recovered by simple phase separation from the cooled effluent. Liquid hydrocarbons consisting essentially of $C_5^+$ gasoline range materials may be recovered or pumped to the higher secondary stage pressure, or optionally recyled to the primary stage reactor. At least a portion of the vapor phase effluent from the primary stage is compressed and heated along with gasoline diluent or throughput liquids to oligomerization reaction temperature, and the combined olefinic stream (optionally containing recycled olefinic gasoline) is reacted at high pressure and elevated temperature over the catalyst. Secondary stage II effluent is then separated into light gases, $C_5^+$ gasoline for recycle in part to Stage I and Stage II, and distillate range products. The distillate stream comprises a major fraction of $C_{10}$-$C_{20}$ high boiling aliphatics and may contain a minor amount of aromatics.

In the process for catalytic conversion of olefins to heavier hydrocarbons by catalytic oligomerization using an acid crystalline zeolite, such as ZSM-5 type catalyst, process conditions can be varied to favor the formation of either gasoline or distillate range products. At moderate temperature and relatively high pressure, the conversion conditions favor distillate range product having a normal boiling point of at least 165° C. (330° F.). Lower olefinic feedstocks containing $C_2$-$C_6$ alkenes may be converted selectively; however, the distillate mode conditions do not convert a major fraction of ethylene. While propene, butene-1 and others may be converted to the extent of 50 to 99% in the distillate mode, only about 10 to 50% of the ethylene component will be consumed.

Alkylation of ethylene with methanol over ZSM-5 catalyst has been described by Kaeding et al (*J. Catalysis*; January 1980, August 1984), and it is known to recycle ethene in the production of aromatic gasoline from methanol over zeolites (U.S. Pat. No. 3,998,899, Daviduk). In a fluidized bed plant for converting methanol to lower olefins and gasoline, recycle of ethylene at a rate of 2.5 parts by weight be 100 parts $CH_2$ equivalent in the feedstock methanol provides a product yield that is substantially the same, as shown in Table I. These continuous runs are conducted at the same conditions.

TABLE I

| | Hydrocarbon Product Yield, Wt % | |
|---|---|---|
| Component | Without Recycle | With ethene Recycle |
| $C_1$ | 0.8 | 0.8 |
| $C_2$ | 0.3 | 0.3 |
| $C_2=$ | 2.5 | 2.7 |
| $C_3$ | 4.4 | 4.5 |
| $C_3=$ | 4.6 | 4.5 |
| $nC_4$ | 2.1 | 2.1 |
| $iC_4$ | 10.8 | 10.4 |
| $C_4=$ | 5.4 | 5.1 |
| $C_5^+$ (Gasoline) | 69.1 | 69.6 |

TABLE I-continued

| | Hydrocarbon Product Yield, Wt % | |
|---|---|---|
| Component | Without Recycle | With ethene Recycle |
| Total | 100.0 | 100.0 |

T = 407° C.,
P = 400 KPa,
WHSV = 2.65 hr$^{-1}$ (based on HZSM-5 catalyst).

Figure 2:
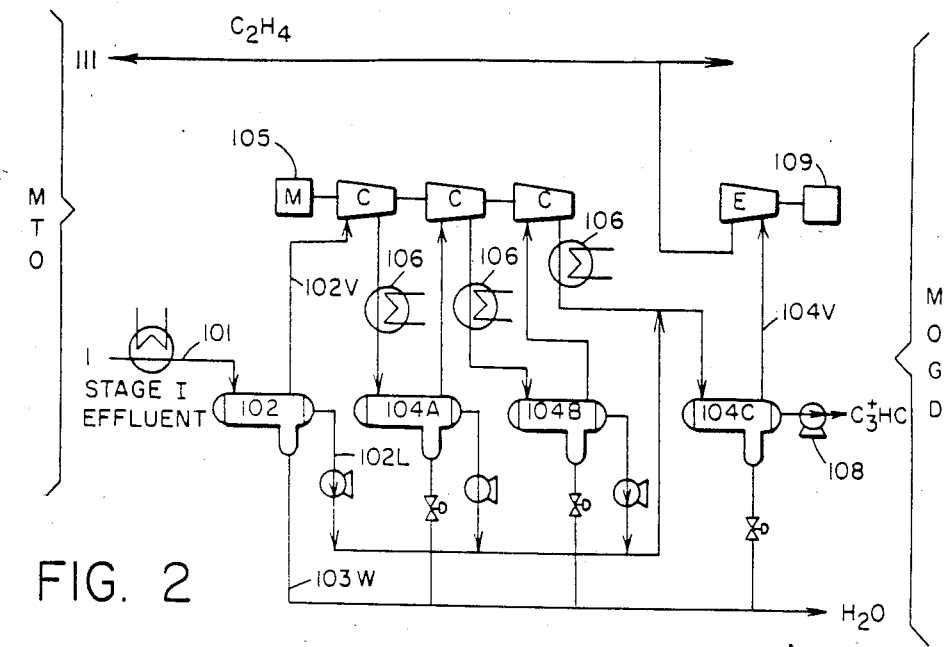
FIG. 2 is a schematic representation of a preferred inter-stage separation system for ethene recovery.

In the embodiment of FIG. 2, the light hydrocarbon vapor stream separated from the primary stage effluent is compressed in a plurality of compression stages to condense liquid olefinic hydrocarbons. The full reaction effluent of the primary stage MTO plant is passed via conduit 101 and primary phase separator 102 to provide a first vapor stream 102V, rich in $C_4$-hydrocarbons, liquid hydrocarbons stream 102L, and by product water stream 103W. The liquid (e.g.-$C_5+$) stream 102L is combined with a corresponding liquid HC from succeeding separators and withdrawn. The primary vapor stream 102V is adiabatically compressed by multi-stage motor-compressor set 105 M-C, cooled via exchanger 106 and passed to a succeeding separator 104A, at which point the preceeding phase separation technique is repeated. Likewise other separators 104B and 104C operate to provide an ethene-rich recycle stream 104V, which is passed to turbo-expander 109E and thus at MTO pressure back via line 111 to the olefins production in the primary stage. Advantageously, the MTO effluent is received at about atmospheric pressure (e.g., 100-150 kPa) and compressed in plural stages to an intermediate pressure of about 1100-3500 kPa (150-400 psig) and separated in the final vessel 104C at about ambient temperature (20°-60° C.). Olefinic liquids rich in $C_3+$ aliphatic are recovered from the final compressor stage via pump 108 which pressurizes the liquid HC stream to sufficiently high pressure to be employed in the following secondary stage MOGD unit.

Figure 3:
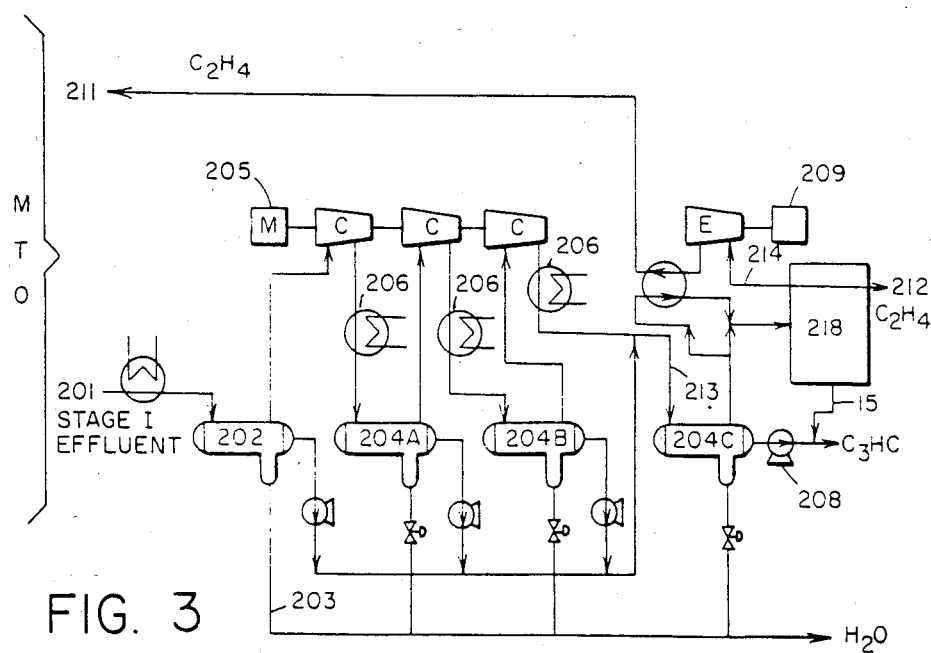
FIG. 3 is a schematic representation of an alternative system.

A further modification of the interstage ethene separation technique described above is depicted in the flow diagram in FIG. 3, wherein corresponding apparatus and process streams are identified by corresponding numbers. In this adaption, ethene-rich vapor withdrawn from the first separator 204C via line 213 is cooled by heat exchanged and further processed to increase ethene purity in ethylene unit 216. As will be understood by one skilled in the art, ethene can be treated in a cryogenic plant cold box, de-ethanizer tower, absorption unit or the like to remove undesirable components prior to recycle 211 and/or recovery 212. A suitable selective sorption unit is disclosed in U.S. Pat. No. 4,471,147 (Hsia et al), incorporated herein by reference. Preferably, compressed light hydrocarbons are fractionated to recover a recycle stream containing at least 90 mole percent ethene. This can be achieved by selectively absorbing $C_3+$ components in a $C_5+$ liquid hydrocarbon sorbent stream.

Figure 4:
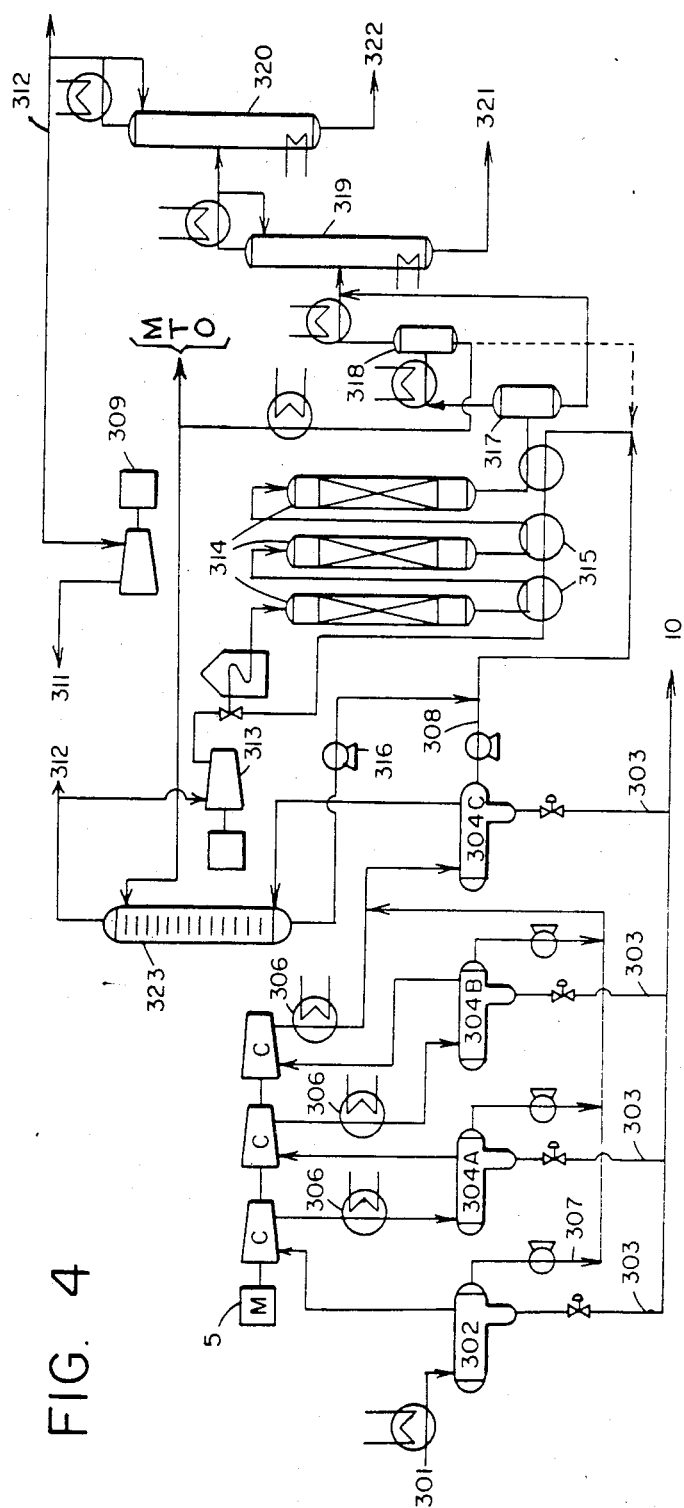
FIG. 4 is a preferred embodiment of an integrated olefins upgrading process, depicted by process flow sheet.

In FIG. 4 a continuous multi-stage catalytic system is depicted for converting oxygenated feedstock to liquid hydrocarbons. The process flow diagram shows an integrated plant. The primary stage includes catalytic reactor means containing acidic zeolite catalyst for converting oxygenate to olefinic hydrocarbons rich in $C_2-C_4$ alkenes. The interstage section includes separation means for recovering water and light hydrocarbon vapor from the primary stage effluent stream, means for pressurizing the primary stage hydrocarbon effluent stream to recover an intermediate hydrocarbon liquid stream rich in $C_3+$ components and an ethene-rich vapor stream. The secondary stage includes catalytic oligomerization reactor means containing medium pore shape selective acidic zeolite oligomerization catalyst for converting the $C_3+$ olefinic hydrocarbons to heavier liquid hydrocarbons. Fractionation means 317, 318, 319, 320 provide towers for separating secondary stage effluent into a light hydrocarbon stream containing $C_2-C_4$ aliphatic hydrocarbons, a $C_5+$ gasoline stream and distillate range stream. By recovering and recycling at least a portion of the gasoline to the primary stage for reconversion, an economic system is achieved. The $C_5$ to $C_9$ gasoline range olefins are coproduced with varying amounts of other hydrocarbons in this boiling range, especially aromatics. While aromatics are not made in large quantity in the MOGD secondary reactor stage due to relatively low operating temperatures, the primary stage MTO reactor can produce significant quantities at further elevated temperatures. By separating the heavier ($C_8+$) aromatics from the MTO effluent, a valuable high octane liquid fuel may be recovered and formation of undesirable byproducts avoided.

Gasoline range hydrocarbons from the secondary stage MOGD effluent typically contain at least 50 wt. % $C_5$ to $C_9$ olefins, with 90% or more mono-alkene being obtainable. These are mostly straight chain or slightly branched mono-olefinic molecules. A large portion of this effluent stream may be recycled to the MOGD reactor system for upgrading to distillate. It is a main object of this invention to reconvert a recycled portion of the MOGD gasoline by introducing it to the primary stage reactor conditions. At the higher temperature (e.g. 475° C.+) the aliphatic hydrocarbons undergo cracking and interpolymerization to produce a widely-distributed equilibration product range comprising $C_2=$, a large fraction of $C_3=-C_4=$, and heavier olefins. Recycled aliphatic hydrocarbon is particularly advantageous in the increasing production of propene and butenes.

In view of the highly reactive nature of methanol/DME or other oxygenate feedstocks, it is preferred to isolate the $C_5+$ recycle reactant stream by introducing it to the MTO reactor substantially downstream from the oxygenate inlet at a point where the oxygenate has been essentially completely converted to hydrocarbons. This feature of the process prevents alkylation of the recycled $C_5+$ components by methanol or the like and optimizes net production of the desirable $C_3-C_4$ olefins. To facilitate the olefinic gasoline equilibrating reactions from oxygenates, a fluidized bed catalytic MTO reactor is satisfactory. A suitable reactor and operating technique is disclosed in copending U.S. patent application Ser. No. 687,045, filed Dec. 28, 1984, by Gould et al, incorporated herein by reference. In the preferred MTO reactor, a bed of finely divided (<150 microns) ZSM-5 catalyst is maintained in a turbulent fluidization regime. Hot feedstock vapor is passed upwardly through the fluidized bed at a superficial velocity of about 0.3 to 2 meters per second, maintaining a bed density of about 100 to 300 kg/m$^2$. Operating at about 520±20° C. and a catalyst activity sufficient to yield a propane: propene ratio of about 0.02 to 0.3:1, production of ethylene can be controlled at a low level.

In the examples below, the aliphatic gasoline recycle stream contains 94 wt% of $C_5-C_9$ olefins, 4% $C_5-C_{10}$ paraffins and 2% $C_6-C_{11}$ aromatics. This recycle stream is produced by a secondary stage oligomerization unit operating at about 5500 kPa, 1 WHSV (based on weight of fresh olefin feed to ZSM-5 catalyst) at 260° C., using the MOGD system of FIG. 4 with 2:1 internal MOGD gasoline recycle. The portion of this gasoline recycled to the primary stage MTO reactor in Case B is introduced at midpoint stratum in the fluidized bed, corresponding to more than 99.5% methanol conversion. In case C the gasoline recycle is combined with the methanol feedstock and introduced at the bottom reactor inlet. Case A is the control run without recycle. The results of three continuous MTO runs is given in Table II, based on 100 parts by weight of hydrocarbon equivalent in the feedstock methanol.

TABLE II

| Material Balance for Aliphatic Gasoline Recycle | | | |
|---|---|---|---|
| | Case A | Case B | Case C |
| $C_1$ | 2.0 | 2.1 | 2.0 |
| $C_2$ | 0.4 | 0.6 | 0.4 |
| $C_2=$ | 5.2 | 7.4 | 6.4 |
| $C_3$ | 2.1 | 3.4 | 3.2 |
| $C_3=$ | 32.9 | 38.2 | 34.0 |
| n-$C_4$ | 0.7 | 1.0 | 1.3 |
| i-$C_4$ | 2.3 | 3.1 | 4.7 |
| $C_4=$ | 19.1 | 22.6 | 20.4 |
| $C_5$+ P + N | 9.1 | 15.1 | 20.3 |
| $C_5$+ O | 19.7 | 21.4 | 20.1 |
| Aromatics | 6.5 | 9.6 | 11.7 |
| | 100.0 | 124.5 | 124.5 |

The above runs are conducted at 500° C., 180 kPa and about 2.1 WHSV. When operating an integrated MTO/MOGD plant according to each of the three cases, A, B, C, above, the net percentage of distillate product is increased by recycling gasoline to the primary stage, as shown in Table III.

TABLE III

| Integrated MTO/MOGD Product Yields | | | |
|---|---|---|---|
| Product Yields, Wt. % | Case A | Case B | Case C |
| Fuel Gas | 2.5 | 2.9 | 2.6 |
| LPG | 4.8 | 6.5 | 7.9 |
| $C_5$ −175° C. Gasoline | 31.7 | 20.0 | 26.0 |
| 175° C.+ Distillate | 61.0 | 70.6 | 63.5 |
| | 100.0 | 100.0 | 100.0 |
| Total gasoline + distillate (G + D) | 92.7 | 90.6 | 89.5 |
| Gasoline Octane (R + O) | 93.2 | 97.5 | 95.1 |

The optimum case B not only increases the distillate yield, but also provides gasoline product of enhanced octane rating. Both cases B and C provide gasoline recycle to the primary stage at a continuous rate of 24.5 parts by weight per 100 parts of hydrocarbon equivalent in the methanol feed. This recycle rate may be varied from about 1 to 30 parts per 100 HC depending on the combined effects of ethene recycle, MOGD operating mode, etc.

When introducing recycle gasoline to the MTO fluidized bed, the recycle stream should be uniformly distributed by injecting vapor or liquid at least 10% up the bed height, preferably 25 to 50% up the bed. It will be understood by one skilled in the art that more than 99% of the methanol can be converted in the initial 25% of the space time interval. Under the conditions described, methanol conversion to lower olefins and recycle equilibration are maintained essentially separate, with less than 1%, preferably less than 0.2% of the methanol remaining unconverted at the point or stratum of recycle injection.

Figure 5:
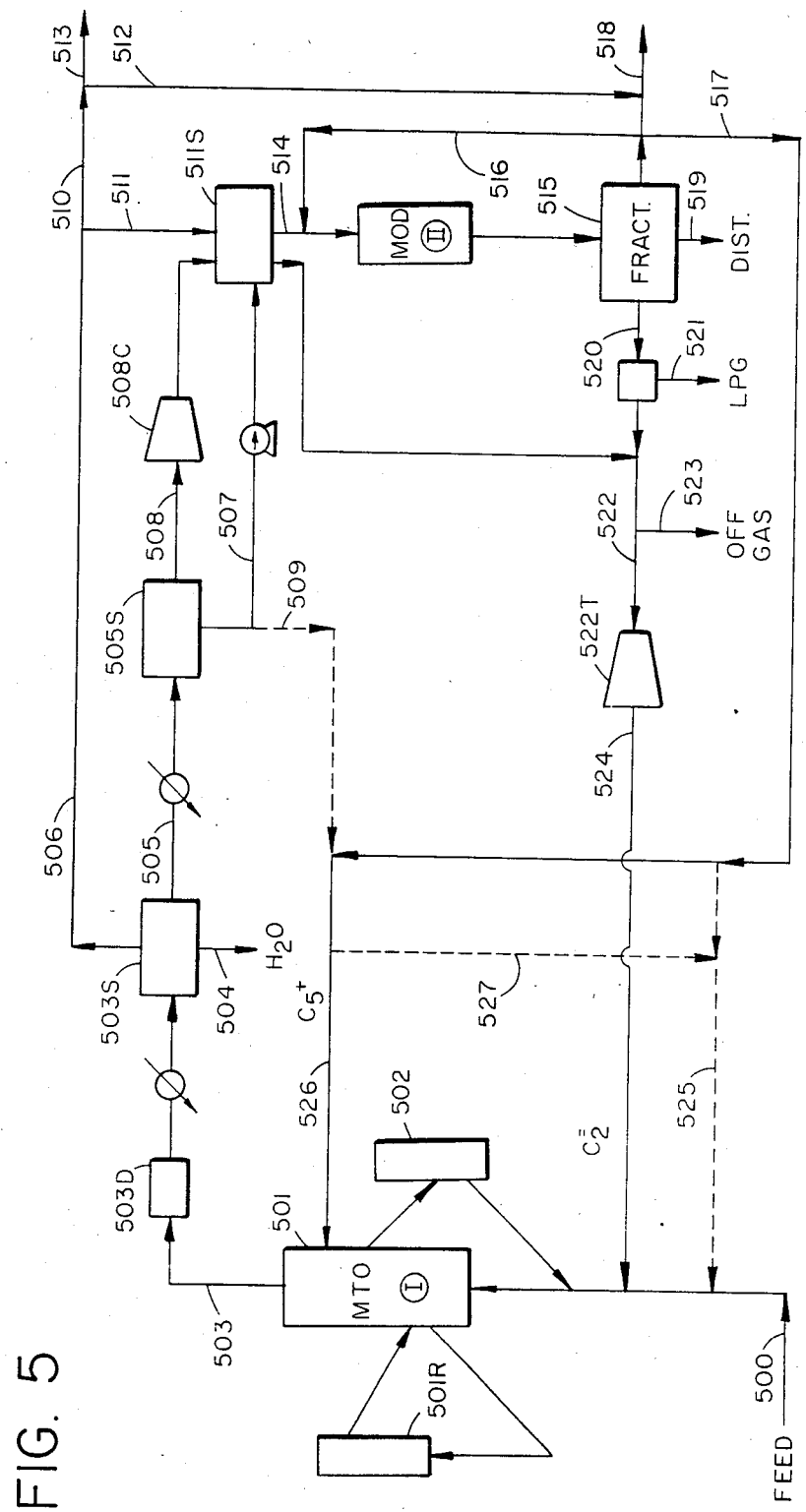
FIG. 5 is an alternative process flow sheet depicting optional integration techniques.

A schematic flow sheet of the system is shown in FIG. 5. Vaporized and/or liquid methanol 500 is fed to the fluid bed Stage I MTO reactor 501. The water content of the feed can be 0–50 wt %, preferably less than 5 wt %. An ethene rich gas stream 524 can be co-fed with the methanol. The main fluid bed reactor can be operated either in the preferred turbulent dense bed mode or as a dilute phase riser reactor. In this example, exothermic heat of reaction is removed in an external cooling vessel 502 by circulating catalyst through transfer lines. Conversion catalyst is circulated continuously to the regenerator vessel 501R.

If maximum distillate production is desired, an aliphatic gasoline recycle stream 526 is introduced as a vapor and/or liquid directly into the fluid bed reactor 501. Location of the injection point is important. The gasoline recycle should first contact the catalyst in a region where the local concentration of unconverted methanol is low (<1 wt %, preferably less than 0.05 wt %) to prevent formation of higher paraffins and aromatics via reaction with methanol.

In the absence of appreciable quantities of methanol, the gasoline recycle stream will equilibrate to a mixture rich in low molecular weight olefins and aromatics. Overall, MTO olefin selectivity will increase with a concommitant increase in stage II distillate production. As an alternative, gasoline recycle streams 509 and 517 may be admixed with fresh methanol feed via conduit 525. The aliphatic/olefinic gasoline so recycled can react with methanol in the MTO reactor 501 to make primarily high octane, aromatic gasoline.

The total MTO product gas stream 503 is cleaned via catalyst separation device 503D, cooled, and separated in vessel 503S into a water stream 504, light hydrocarbon vapor 505 and condensed aromatic gasoline 506 fractions. The heavy gasoline 506 can be fed to the Stage II distillate mode MOD reactor via lines 511 and 514, combined with recycle gasoline 516 via line 512, or isolated as a final product 513. The light hydrocarbon vapor stream 505 is cooled further and separated in unit 505S into liquid 507 and light gaseous 508 hydrocarbon streams. Liquid hydrocarbons from the low temperature separator 505 are pumped to the Stage II reactor via high pressure separator 511S and/or recycled to the Stage I MTO reactor via line 509. The light hydrocarbons are compressed 508C and sent to the high pressure separator 511S. The pressure and temperature of the separator are chosen so that ethane, ethene, and lighter compounds are in the gaseous phase while the $C_3$+ fraction is a liquid. The olefinic liquid hydrocarbons 514 are combined with gasoline recycle stream 516 and pumped to the Stage II fixed bed reactor system. Hydrocarbon gas stream 522, which is predominately ethene, is recycled to the inlet of the fluid bed reactor 501 after energy recovery in a turboexpander 522T. The secondary stage fractionation system 515 is operated in a conventional manner to produce LPG, gasoline range, and diesel range products, (streams 521, 518, 519, respectively) except that a fraction of the LPG rich, $C_2$-containing off-gas may be recycled back to the fluid bed reactor 501 via turboexpander 522T. Purge gas stream 523 is sent to a fuel gas plant to prevent the build-up of paraffins in the recycle loop.

The combined processes are an effective means for converting oxygenated organic compounds, such as methanol, DME, lower aliphatic ketones, aldehydes, esters, etc, to valuable hydrocarbon products. Thermal integration is achieved by employing heat exchangers between various process streams, towers, absorbers, etc.

Various modifications can be made to the system, especially in the choice of equipment and non-critical processing steps. While the invention has been described by specific examples, there is no intent to limit the inventive concept as set forth in the following claims.

What is claimed is:

1. A process for converting oxygenate feedstock comprising methanol, dimethyl ether or mixtures thereof to predominantly distillate range liquid hydrocarbons comprising the steps of contacting the feedstock with zeolite catalyst in a primary fluidized bed catalyst stage at elevated temperature and moderate pressure to convert feedstock to hydrocarbons comprising $C_2$–$C_4$ olefins and $C_5+$ hydrocarbons;

cooling and separating effluent from the primary stage to recover a liquid hydrocarbon stream and a light hydrocarbon vapor stream rich in $C_2$–$C_4$ olefins;

pressurizing and contacting the light olefinic hydrocarbon stream in a secondary catalytic stage with oligomerization catalyst comprising medium-pore shape selective acidic zeolite at substantially increased pressure and moderate temperature to convert at least a portion of olefins to a heavier liquid hydrocarbon product stream comprising olefinic gasoline and distillate range liquids; and injecting at least a portion of the olefinic gasoline recycle stream into the fluidized catalyst bed of the primary stage reactor at a separate point above the oxygenate feedstock.

2. The process of claim 1 wherein primary stage feedstock is converted over HZSM-5 catalyst to provide a light olefinic hydrocarbon vapor stream comprising a major amount of $C_3$–$C_4$ olefins and a minor amount of ethene.

3. The process of claim 1 further comprising the step of fractionating gaseous effluent separated from primary stage effluent to recover a recycle gas stream containing at least 90% of ethene from the primary catalytic stage and an olefinic stream rich in $C_3+$ olefins.

4. The process of claim 1 wherein the primary and secondary stage catalyst comprises ZSM-5 type zeolite and olefinic gasoline is recycled to the primary stage at a rate of about 1 to 30 parts gasoline per 100 parts by weight of hydrocarbon equivalent in the feedstock.

5. The process of claim 1 wherein compressed light hydrocarbon gaseous stream is further fractionated by selectively absorbing $C_3+$ components in a $C_5+$ liquid hydrocarbon sorbent stream.

6. The process of claim 5 wherein a $C_5+$ fraction of the secondary stage liquid hydrocarbon product stream comprising olefinic gasoline is recycled as the sorbent stream.

7. A process for converting oxygenated feedstock to liquid hydrocarbons comprising the steps of contacting the feedstock with fluidized bed catalyst in a primary catalyst stage at elevated temperature and moderate pressure to convert feedstock to hydrocarbons comprising $C_2$–$C_4$ alkenes and $C_5+$ hydrocarbons;

cooling and separating effluent from the primary stage to recover a liquid hydrocarbon stream and a light hydrocarbon stream rich in $C_2$–$C_4$ alkenes;

compressing the light hydrocarbon stream to condense a liquid olefinic hydrocarbon stream rich in $C_3+$ alkenes and recovering an ethene-rich gaseous stream;

further pressurizing and contacting the condensed liquid olefinic hydrocarbon stream in a secondary catalytic stage with oligomerization catalyst comprising medium-pore shape selective acidic zeolite at substantially increased pressure and moderate temperature to convert at least a portion of alkenes to a heavier liquid hydrocarbon product stream comprising olefinic gasoline and distillate range liquids; and recycling a lower alkene stream recycle to the primary catalytic stage.

8. The process of claim 7 where at least a portion of the alkene recycle stream is gasoline recovered from the secondary stage liquid effluent hydrocarbon stream, said gasoline containing at least 50 weight percent $C_5$ to $C_9$ olefins.

9. The process of claim 7 wherein the recycle comprises $C_5+$ hydrocarbons recovered between the primary and secondary stages.

10. The process of claim 8 wherein the alkene recycle stream is injected into the fluidized catalyst bed of the primary stage reactor at a point above the oxygenate feedstock charge.

11. The process of claim 7 wherein the alkene recycle stream is injected above a bed stratum corresponding to at least 99% oxygenate conversion.

* * * * *